United States Patent
Cui et al.

(10) Patent No.: US 8,684,928 B2
(45) Date of Patent: Apr. 1, 2014

(54) VITALIMETRICS-BASED METHODS, DEVICES AND SYSTEMS FOR HEALTH/LIFESTYLE MAINTENANCE AND IMPROVEMENT

(76) Inventors: Zhiqiang Cui, Elmhurst, NY (US); Matthew Lee, Conroe, TX (US)

( * ) Notice: Subject to any disclaimer, the term of this patent is extended or adjusted under 35 U.S.C. 154(b) by 3 days.

(21) Appl. No.: 13/245,842

(22) Filed: Sep. 26, 2011

(65) Prior Publication Data

US 2012/0083672 A1    Apr. 5, 2012

Related U.S. Application Data

(60) Provisional application No. 61/386,546, filed on Sep. 26, 2010.

(51) Int. Cl.
*A61B 5/00*    (2006.01)

(52) U.S. Cl.
USPC .......................................... 600/301

(58) Field of Classification Search
None
See application file for complete search history.

(56) References Cited

U.S. PATENT DOCUMENTS

| | | | |
|---|---|---|---|
| 5,050,613 A * | 9/1991 | Newman et al. | 600/483 |
| 8,332,027 B2 * | 12/2012 | Larsen | 600/548 |
| 2004/0181159 A1 * | 9/2004 | Kuo et al. | 600/509 |
| 2009/0124914 A1 * | 5/2009 | Kuo et al. | 600/500 |
| 2009/0326391 A1 * | 12/2009 | Chan et al. | 600/490 |
| 2010/0222697 A1 * | 9/2010 | Larsen | 600/548 |
| 2011/0319774 A1 * | 12/2011 | Wu | 600/490 |
| 2012/0265081 A1 * | 10/2012 | Wu | 600/490 |

* cited by examiner

*Primary Examiner* — William Thomson
*Assistant Examiner* — Shirley Jian

(57) ABSTRACT

This invention provides methods and devices for vitalimetrics-guided health/lifestyle and improvement.

9 Claims, 3 Drawing Sheets

VITALIMETRICS-BASED METHODS, DEVICES AND SYSTEMS FOR HEALTH/LIFESTYLE MAINTENANCE AND IMPROVEMENT

CROSS-REFERENCE TO RELATED APPLICATIONS

This application claims the benefit of U.S. Provisional Application No. 61/386,546, file on Sep. 26, 2010. The above application(s) is hereby incorporated herein by reference.

FIELD OF THE INVENTION

The invention pertains generally to the field of vitalimetrics. In particular, the present invention relates to methods and tools for vitalimetrics-guided health/lifestyle maintenance and improvement.

BACKGROUND OF THE INVENTION

Darwin's theory of evolution has proven to be extremely useful in explaining the evolution of species and has provided a framework for us to understand life at the species level. With the advances of molecular biology in the past 30 years, we now understand that life on earth is essentially the interplay between the genetic code and the environment. It is now well accepted that whenever there is major environmental change, mass extinction ensues to clear out the unfit species and make way for new species that are better adapted to survive in the new environment. Like all living organisms on earth, we human have also evolved through the ages as a result of evolutionary pressure placed on our genome by environmental factors. Hence, human body as it exists today is the product of the environment; it has been evolved to be optimally suited for a certain set of environmental conditions that has dominated earth for the past few million years.

Given that the human body has been evolved to suit a certain kind environment, it stands to reason that human health is inextricably linked to its surrounding environment. However, our understanding of the environmental effects on health is still very poorly developed. Modern medicine largely ignores the effects of the environment and takes the view that the human body is more like a machine than an integral part of the environment and human diseases are best treated by "fixing" the broken parts. For example, we only see cancer as a cellular dysfunction which manifests as out-of-control cell growth, but we fail to explain why cells grow out of control. All mainstream cancer therapies aim to eradicate these aberrant cells, but we know that cutting out the cancerous cells do not guaranty a cure. On the other hand, we know that there are cancer patients who spontaneously heals without any medical intervention. In many such cases, the patients often attribute the miraculous healing to change in their lifestyles, living conditions, and mental attitudes.

At a conceptual level, spontaneous healing claims are not completely without logics. The phrase "under the weather" suggests that our ancestors have long recognized the important links between the environmental factors and our health. Among the environmental factors, levels of solar radiation, atmospheric temperature, surface temperature, wind, atmospheric pressure, altitude, etc. all have immediate and observable effects on our body and mental states. For example, if the temperature is too high, we will sweat and lose water. If the air is too dry, our skin will crack. These are extreme environmental conditions that can produce an immediate result in our body. But what about less extreme changes in the environment? We know that human body has evolved over millions of years to its current form. The environment has more or less stayed the same for the past few millions of years for us. But in the past hundred years, through industrialization, we have drastically altered our own environment. We have become less active, exposed ourselves to far more sensory stimulations then our ancestors, and fed our bodies foods that were not readily available to our ancestors. Our bodies have not had time to adjust to these sudden environmental changes and we are just beginning to notice their impact on our health. For example, in the U.S., the link between obesity and fast food is now well recognized.

Another important environmental change is global warming. From 1981 to 1990, the temperature of earth has risen 0.48° C. This number may seem insignificant at first, but when we recognize that this change is here to stay, we must ask what impact will this have on our health over the long term.

To answer these questions, tools for collecting data about human health and the environment as well as methods for analyzing the data are needed. More importantly, to maintain human health, devices that can provide input about the body's state of health and the environmental conditions will be very useful.

SUMMARY OF THE INVENTION

In view of the foregoing, it is an object of this invention to provide methods, devices, and systems for monitoring a person's state of health concurrently with the environmental conditions.

It is also an object of this invention to provide methods, devices, and systems for quantifying a person's state of health concurrently with the environmental conditions.

It is still another object of this invention to provide methods, devices, and systems for maintaining and improving the health and lifestyle of a person utilizing information about his state of health and the concurrent environmental conditions.

At the heart of this invention is the unexpected discovery that the variation of vital sign values such as temperature, pulse rate, blood pressure, and etc. taken from symmetric counter-parts of a patient's body shows patterns in diseased states which can be influenced by environmental conditions. Accordingly, inventors have devised a method for quantifying a person's state of health based on his symmetric vital signs and the concurrent environmental conditions. Based on this method, various devices and systems for utilizing the method to monitor, maintain, and improve a person's health are also devised.

As used herein, the phrase "vital sign" refers to any quantifiable physiological, psychological, or biochemical variables that can be shown to indicate life processes. Commonly known vital signs may include body temperature, pulse rate, blood pressure, concentration of metabolites, or biomegnatic field, but are not limited thereto.

As used herein, the phrase "symmetric counter-parts of a patient's body" refers to any partitioning of anatomical parts that have a symmetric counter-part. Exemplary symmetry counter-parts include up-down, left-right, and anterior-posterior, For example, left-hand and right-hand, left-leg and right-leg, left-ear and right-year are all considered symmetric counter-parts in the context of the present invention.

As used herein, the phrase "symmetric health" refers to a person's state of health as indicated by his symmetric vital signs.

As used herein, the term "vitalimetrics" refers to the study and application of body vital sign information.

As used herein, the phrase "environmental condition" refers to any measurable physical parameters external to the subject of interest. For example, if the subject of interest is a person, then any physical parameters such as atmospheric temperature, levels of solar radiation, noise level, etc. are all considered environmental conditions.

One essential feature of the present invention is that human health is viewed in conjunction with environmental as a holistic system. However, modern western medicine is build on the foundation of anatomy and advances its knowledge by isolating the body from the environment. Thus, modern western medicine is ill suited to account for environmental factors. On the other hand, while there are numerous independent systems of medicine that subscribes to a holistic view of human health, most of them are based on qualitative, philosophical reasonings and lack a theoretical foundation capable of quantitative analysis and experimentation. Among the various systems of holistic medicine, traditional Chinese medicine (TCM) is arguably the most developed in terms of theory. Using TCM as an example, inventors have devised an approach to bridge the soft philosophical views of holistic medicine with the hard empirical views of modern western medicine.

While not intending to be bound by any theory, we believe that an analogy to the relationship between thermodynamics and the atomic theory may help to facilitate a full understanding and appreciation of the discovery forming the basis of the present invention.

As it is now commonly understood by students of modern science, scientific theories are merely mental models we constructed to represent the reality as we know it. The theory of thermodynamics was developed before the discovery of atoms, thus, it was framed in the macroscopic observables of matter, such as temperature, pressure, and volume. From observation of these macroscopic variables under different conditions, the concepts of system and energy were introduced and laws concerning their behaviors were proposed. For example, in describing a bucket of water, thermodynamics knows nothing of atoms and molecules but describes the bucket of water as existing in a state defined by its temperature, pressure, and volume. Although devoid of any understanding and description of the structures of matter, thermodynamics has been tremendously useful and successful in explaining and predicting natural phenomena at the macroscopic scale.

Later, when the atomic structure of matter was discovered, scientists began to explain the universe in terms of atoms. In the nineteenth century, the famous French astronomer Pierrer-Simon Laplace put forth the concept that if we can know all forces acting on each particle in the universe and the position of each particle at a given time, we can predict the entire history—future and past—of the universe. In the above bucket-of-water example, atomic theory now sees the bucket of water as a collection of water molecules in random motion. Yet, knowledge of the atomic structure did not readily translate into understandings of phenomena at the macroscopic scale. Everyday experiences such as the boiling temperature of the water could not be readily derived from a full atomistic description of the composition of water. In this respect, thermodynamics remained much more useful as a theory for explaining phenomena at the macroscopic scale.

These two theories view the world from different perspectives and sought to describe the world from their respective views. Now imagine someone who has only learned of the thermodynamics theory meeting someone who has only learned of the atomic theory. Each would likely criticize each other's view of the universe and easily find faults in each other's theories. But despite the vastly different language and logical structure of the two theories, they both explain the same underlying reality. Therefore, there must be a missing link between the thermodynamics theory and the atomic theory. Indeed, it was not until the invention of a new theory—statistical mechanics—that finally united these two previously disparate views of the physical world. Through statistical mechanics, the macroscopic variable, temperature, was finally explained as the average kinetic energy of the collective atoms in a bulk material.

The inventors posit that the situation between modern western medicine and holistic medicine are very similar to that of the thermodynamics theory and the atomic theory. Western medicine is fundamentally based on the reductionist view of human body. That is, it views the human body as a collection of ever finer components (e.g. organs, tissues, and cells) and diseases as structural or functional aberrations of the components. In this sense, Western medicine is analogous to the atomic theory.

In contrast, holistic medicines such as TCM are based on a systems view of the body. That is, it views the human body as a system in dynamic interaction with its environment. When the theories of TCM was developed, detailed knowledge of the anatomical components was clearly not available. Thus, the theoretic paradigm of TCM is based on observations of systems behaviors and views disease states as deviation of the system from its native state. All deviations are then described as directional deviations either in the negative (yin) or positive (yang). For example, a person presenting with strong pulse, red body, red face, Western medicine may describe the patient as suffering from hypertension whereas TCM may describe the patient as having excess yang. Here hypertension is a readily quantifiable mechanical property of the component whereas yang is an abstract systems variable that lack a direct translation in the language of the components. In this sense, TCM is analogous to the thermodynamics theory.

In keeping with the systems view, TCM further postulates that any diseased state can be understood as an imbalance in the patient. TCM recognizes many patterns of disharmony, which are succinctly grouped into eight principle patterns composed of four opposites: internal/external, hot/cold, full/empty, and yin/yang. These eight variables are known as the "Eight Principles." The Eight Principles is the basic diagnostic paradigm in TCM as it shows the location and nature of imbalance. Using the Eight Principles, one learns the characteristics of the presenting imbalance. Thus, TCM's medical theories provide a logical framework to organize empirical knowledge accumulated at the systems level.

Although useful as a thinking tool, the Eight Principles relies on individual practitioner's subjective judgment for determination and lacks quantitative rigor. Because of the fundamental differences in the perception of individuals, transfer of knowledge and techniques between Western medicine and TCM have heretofore been difficult. What is lacking then is a third theory skin to statistical mechanics that can provide a bridge between the qualitative systems view of TCM and the quantitative components view of Western medicine. Unfortunately, the Eight Principles have thus far eluded quantification.

Through extensive clinical observations and experimentations, the inventors have discovered the "missing link". In particular, we propose herein an approach to quantitatively analyze systems behavior of a patient and correlate vital sign information along with concurrent environmental conditions to a person's state of health. Accordingly, methods of this invention may serve as a new quantitative interpretation for the Eight Principles by relating quantifiable vital signs of the patient to the Eight Principles.

To better appreciate the conceptual breakthrough of this discovery and its practical implications, we invite the reader to conceptualize a vitality space defined by variables that may be thought of as state variable for a person's state of health. In one exemplary embodiment, the four opposites of the Eight Principles may be used as four state variables to form a four-dimensional space in which an infinite number of points exist representing the infinite possibilities of health states of a person. However, as mentioned above, because TCM was developed as a qualitative science, no framework for quantifying the Eight Principles was ever developed. Here we solve this problem by quantifying the dimensions of the Eight Principles in terms of vital sign measurements.

A patient's health state at any given point in time may be represented by a point in the vitality space. Thus, for the purpose of the present invention, we will henceforth refer to this point as the patient's vitality state.

For any living person, his vitality state is in constant motion within the vitality space as a result of the various forces (both internal and external) acting on the patient. The velocity by which the vitality state moves may be represented by a vector, which will be referred to herein as the vitality vector.

In this new paradigm, a patient's health status may be characterized by his vitality state derived from vital sign measurements. Because the quantifiable vital signs are also used in western medicine to characterize disease states, such characterization provides a linkage between the reductionist view of western medicine and the systems view of holistic medicines.

Having arrived at this discovery, numerous applications may be derived therefrom. Exemplary applications may include methods for diagnosing diseases, methods for monitoring health status, methods for treating diseases, methods for maintaining health, and methods for conducting biomedical research. Other medical and non-medical applications utilizing the discovery of the present invention are also possible.

Similarly, devices, systems, and kits for implementing the various methods of the present invention may also be advantageously devised.

Accordingly, in one aspect, the present invention provides methods for classifying, diagnosing, monitoring, and treating diseases. Methods in accordance with this aspect of the present invention will generally include the steps of concurrently measuring one or more symmetric vital signs and one or more environmental conditions; determining a vitality state based on the symmetric vital signs and the environmental conditions; and determining a diagnosis based on the vitality state.

In another aspect, the present invention also provides devices for concurrently monitoring symmetric vital signs and environmental conditions. Devices in accordance with this aspect of the present invention will generally include sensors for concurrently measuring symmetric vital signs and environmental conditions. They will also preferably include means for digitally communicating the measurements via wireless medium.

In another aspect, the present invention also provides computer-implemented systems for monitoring, treating, and maintaining a person's state of symmetric health.

Other aspects and advantages of the invention will be apparent from the following description and the appended claims.

DETAILED DESCRIPTION

Symmetric Vital Signs

Figure 1:
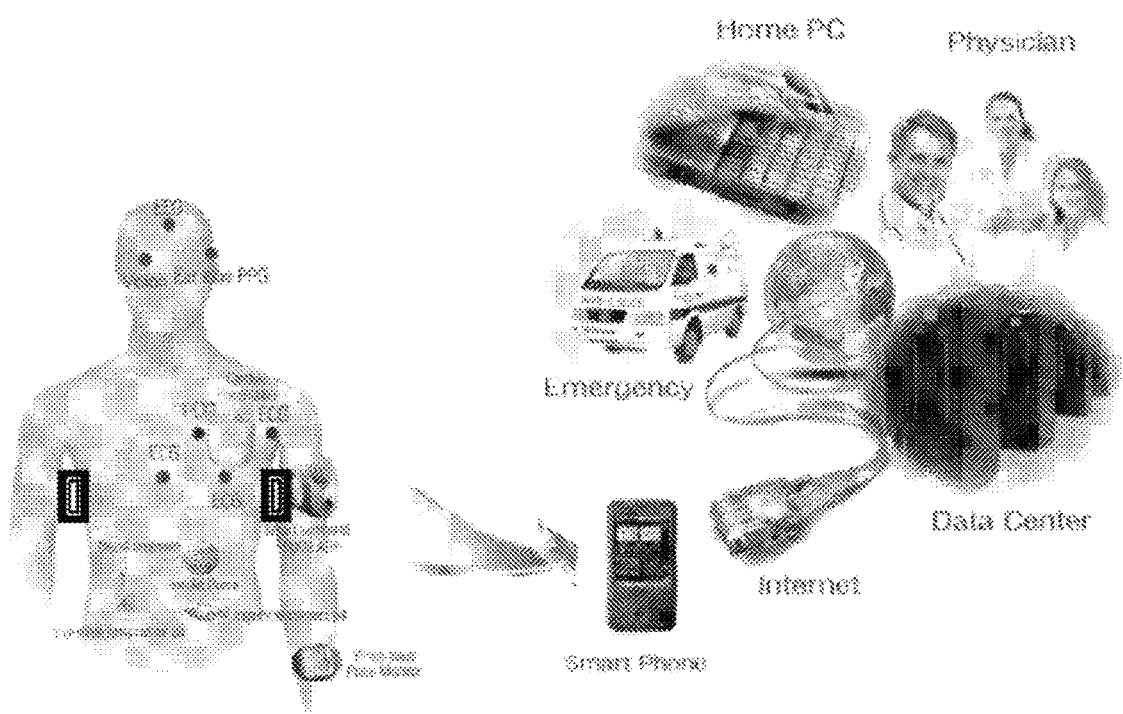
FIG. 1 shows an exemplary symmetric vital sign measuring device in accordance with embodiments of the present invention.

As defined in the summary, the phrase "vital sign" is used to refer to any quantifiable physiological, psychological, or biochemical variables that may be shown to indicate life processes. Common vital signs may include temperature, blood pressure, pulse rate, respiration rate, oxygen consumption rate, and pain, but are not limited thereto.

The phrase "symmetric vital signs", as used herein, refers to the difference of vital sign values taken concurrently from symmetric counter-parts of a patient's body.

Symmetric vital signs can be viewed as the basis for quantifying vitality states.

While not intending to be limited, the concept of symmetric vital sign may be rationalized by considering that human body have many symmetric counter-parts that perform substantially the same function. For example, there are two kidneys, two lungs, two ears, two eyes, two arms, and two legs that perform substantially the same function. In view of this symmetry, it is expected that vital signs measured at the corresponding counter-parts should be substantially the same. This is why when taking the body temperature of a patient, Western practitioners do not make the distinction between whether the thermometer is placed under the right-armpit or the left-armpit.

From previous clinical observations, the inventors discovered that vital signs taken from symmetric counter-parts do show differences under certain conditions, particularly in sick patients. In envisioning the present invention, the inventors made the bold mental leap that vital sign differences in the symmetric counter-parts may be a reflection of the underlying imbalance of the life processes. The inventors further postulate that this quantifiable difference (symmetric vital sign) may be used as a surrogate variable in place of the unquantifiable Eight Principles of TCM. In doing so, the inventors have created a theoretical framework to "quantify" the abstract conceptions of the Eight Principles, thereby, creating a new science of quantitative TCM.

Based on this formulation, a patient's vitality state can finally be quantified and estimated through the use of symmetric vital signs. That is, symmetric vital signs taken at a particular time may be viewed as a snapshot of the patient's vitality state. In this formulation, the vitality state is a system-wide holistic indicator that summarizes the underlying component-level life processes.

Methods for Diagnosing, Monitoring, and Treating Diseases

Methods for diagnosing diseases in a patient utilizing the discoveries of the present invention will generally include the steps of measuring symmetric vital sign differences of one or more symmetric vital sign; determining a vitality state based on the symmetric vital sign differences; and determining a diagnosis based on the vitality state.

The step for measuring symmetric vital sign differences is as described above. In should be noted that for best result, the vital sign readings are preferably taken under a controlled environment, keeping as many conditions constant as possible. For example, readings taken on different days should be taken at about the same time during the day, at about the same ambient temperature, and the patient should be kept at about the same level of activeness.

Similarly, methods for monitoring a patient utilizing the discoveries of the present invention will generally include the steps of measuring symmetric vital sign of one or more vital signs; determining a vitality state based on the symmetric vital sign differences; and repeating the above steps at a predetermined time interval.

Treatment methods utilizing the discoveries of the present invention will generally include the steps of measuring symmetric vital sign differences of one or more vital signs; determining a vitality state from the symmetric vital sign differences; and prescribing a treatment based on the vitality state.

New Disease Classification and Methods for Conducting Research

The discovery of the present invention opens the door for very intriguing new areas of search. Instead of focusing on the material nature of the human body, we aim to discover the logical patterns of behavior through quantitative analysis of vital signs. In other words, instead of describing a human body as a collection of individual cells, and seeking to understand the emergent behavior of the collective by deducing from knowledge of the individual components, we seek to understand directly the logical structure of the collective's behavior without relying on knowledge of its underlying material nature. Since the primary experimental method is by means of quantifying the vital signs to determine the vitality state of a patient, one may refer to this new science as "vitalimetrics".

In particular, a new disease classification system may be created according to the association between vitality states and the pathological conditions. Although this research method may stand on its own as an independent field of inquiry, one advantage of this approach is its ability to bridging the systems view of traditional Chinese medicine with the components view of Western medicine.

To illustrate this concept by analogy, modern research into brain function utilizes MRI imaging to observe the brain activities of the subjects while they are performing various mental activities. By correlating the pattern of the MRI images to the mental activities, the functions of the brain may be described in terms of the MRI image patterns.

Similarly, the vitality states may serve a similar function. By tracking vitality states of subjects under various environmental conditions, disease states, or mental activities, a new language of medicine may be created in terms of the dynamic patterns of the vitality states associated with the conditions.

Hence, in one aspect, the present invention also provides a method of conducting research comprising the steps of determining a vitality state of a subject under a predetermined experimental conditions; and identifying an association between the vitality states with the experimental conditions.

The predetermined experimental conditions may be any set of experimental variables chosen by an investigator depending on the investigator's interest. For example, patients having similar medical conditions and history (e.g. diabetics) may be chosen as the condition for study. The vitality states of these subjects may be followed over a period of time to provide a data source for statistical and pattern analysis. The results of the analysis may have many uses including serving as a basis for formulating health advices or diagnostic tests.

Devices for Measuring Symmetric Vital Signs and Environmental Conditions

The adoption of quantitative methods in western medicine allowed it to benefit from advances in technology. The lack of quantitative methods in holistic medicine such as TCM is a major obstacle for their technological development. In this regard, the symmetric vital sign approach to quantifying vitality states offers a framework to quantify holistic medicine theories. Hence, quantitative instrumentations for holistic medicines, including TCM, can now be developed.

Devices useful for measuring symmetric vital signs will generally satisfy the requirement of reading vital signs from symmetric counter-parts of a patient's body at substantially the same time. Sensor technologies, transducers, and other commonly known biomedical sensing instrumentations may be configured to meet this requirement.

It should be noted that one major challenge of contrasting monitoring devices that are capable of measuring vital signs from symmetric counterparts is that the sensors must have very low error tolerance because the measures must be compared quantitatively to arrive at a difference value for the symmetric vital sign reading. That is, each matching pair of sensors must be calibrated so that their precisions do not create false results.

Methods for Remote Delivery of Holistic Healthcare

As discussed in the background, one major obstacle preventing holistic medicine such as TCM from technological advancements is due to its lack of quantitative foundation for standardization and industrialization. The methods and devices described herein offer a solution to overcome this obstacle in the prior art. As illustrated in one working example below, the quantitative methods described herein are amenable to internet implementation, thereby, bringing TCM to the e-commerce and telemedicine arena.

EXAMPLES

Determination of Vitality States and Disease Monitoring

FIG. 1 shows an exemplary setup for various sensors that may be used to monitor the vital signs of a person. Unlike conventional sensors, these sensors are configured to be capable of measuring vital signs from symmetric counter-parts concurrently as indicated by the placement of the black boxes under each of the armpit. The sensors include both vitality sensors and environmental sensors. These sensors may also be configured to incorporate communication capabilities, thereby, forming a body sensor network. The body sensor network in turn communicates with a long range communication device such as a smartphone. The communication device in turn is capable of processing the received data or relaying the data to a remote processing center via wide-area network such as the internet. The processing center continuously monitors and process the data uploaded and then takes action if needed. For example, if the sensors indicate that the person is in need of medical attention, an emergency response team may be dispatched.

The device of FIG. 1 may also be configured to take readings of pulse rate, blood pressure, pulse pressure, skin electric impedance, and other physiological parameters.

The subject is usually placed in a quiet environment, the vital sign readings are taking every day at the same time for ten days. Care is taken to ensure that the time during the day for each vital sign measurement do not vary more than one hour. To ensure the quality of the data, the subject is asked not to eat or drink two hours prior to the measurement.

Symmetric vital sign is computed by calculating the difference between the readings from, for example, the right-hand side and the left-hand side. This difference represents the vitality state of the patient. A larger vital sign difference indicates that the patient is in a more imbalanced vitality state.

Readings from the first 10 days are time-average and used as a base-line reading. To help visualize the data, the vital sign readings may be plotted on a time-series graph in which the x-axis represents time and the y-axis represents the vital sign readings.

After the base-line is established, vital sign readings are continued to be taken in the same manner, and data from every 10-day period are time-averaged and compared to the base-line. In general, when the vital sign difference is reduced, this will indicate a return to a more balanced vitality state, and vice versa. However, as systems behavior can sometimes show a whip effect, clinical judgment must be used to determine the validity of the change.

Symmetric vital sign measurements are used to construct a multidimensional hyperspace which represents the possible states of a person's health. Mathematical analysis can then be performed on this hyperspace to derive quantitative information about the person's health. In one preferred embodiment, vital signs corresponding to TCM's Eight Principles are measured. As stated above, TCM recognizes many patterns of disharmony which are group into the Eight Principles composed of four pairs of opposites: yin/yang; intern/external; full/empty; and hot/cold. Conceptually, these four pairs form a four-dimensional space for describing the state of health herein referred to as the vitality state. However TCM conceived of these patterns only as qualitative concepts without providing any direct means of measurement.

In this embodiment, we propose using symmetric vital signs as a quantification tool to quantify these basic variable of TCM that characterizes the vitality state of a person.

For example, to quantify and evaluate the vitality state using temperature readings, the temperature differences are assigned in accordance with the yin-yang assignment set forth in the Yellow Emperor's Internal Classic: up is yang, down is yin, left is yang, right is yin. The temperature differences ($\Delta T$) are calculated by subtracting the right-hand side temperature ($T_L$) from the left-hand side temperature ($T_R$), as shown in the following equation:

$$\Delta T = T_L - T_R$$

If $\Delta T$ is positive, then the vitality state is said to be in a state of "excess yang". If $\Delta T$ is negative, then the vitality state is said to be in a state of "excess" yin. If $\Delta T$ is positive, then the vitality state is said to be in a state of "excess" yang. Other vital sign differences are also similarly assigned. In this way, all disease conditions may be classified as deviating from a centered vitality state, either in the direction of excess yang (left-hot/right-cold) or excess yin (left-cold/right-hot).

Depending on the vital sign, a tolerance may be chosen by the physician. For instance, when temperature is measured in degrees Celsius, a tolerance of 0.2 is used. In other words, if the absolute value of $\Delta T$ ($|\Delta T|$) is less than 0.2° C., then the patient is said to be in balanced state of vitality.

When symmetric vital signs are taken in the manner as prescribed above, healthy people will exhibit a balanced vitality state. The greater the imbalance, the more serious the disease. When $|\Delta T|$ is greater than 1.0° C., fatality is imminent.

Within the 10 day observation period, the day on which the maximum $|\Delta T|$ value is observed carries a special significance. Traditional Chinese theory teaches correlation between the lunar cycle and the cycles of the internal organs. We have found that the day of the maximum $|\Delta T|$ in the cycle also indicates a deficiency in the organ (as defined in the Yellow Emperor's Internal Classic) that corresponds to that day. This information is also useful in tailoring a personalized treatment regimen for the patient.

This principle similarly applies to other types of symmetric vital signs.

By tracking the vitality state when a patient is undergoing treatment, the patient's state of health and the effect of the treatment may be continuously monitored.

Binary Classification of Disease States

When measuring symmetric vital signs, the two counterparts will be assigned positive and negative. In general, up is positive, down is negative, left is positive and right is negative. Based on measurements of symmetric vital signs, all disease can be classified into one of two categories: type 1 imbalance (positive imbalance) or type 2 imbalance (negative imbalance). For example, when left-side body temperature is higher than right-side, the person is said to have type 1 imbalance, and vice versa. In this way, all disease states can be classified into one of these two types. One important clinical implication of this classification system is that patients who suffer from diabetes may not all suffer from the same type of imbalance. Hence, their treatment under the present invention will also be different.

Application in the Prediction of Stroke-caused Paralysis

Stroke often causes paralysis in patients on one side of the body. However, it is thus far difficult to predict when stroke will occur or which side of body will become paralyze.

We have discovered that whichever side exhibits excess "hot", that is the side that will become paralyzed. Thus, if a patient is in a state of excess yang (left-hot/right-cold), he will suffer paralysis on the left side of the body when stroke occurs, and vice versa. Therefore, the side of paralysis in a patient prior to the occurrence of stroke may be predicted based on a determination of the patient's vitality state. A useful threshold for $|\Delta T|$, in this case is 0.4° C.

Application in the Prediction of Likely Location of Cancer

Using the diaphragm as a dividing line, the portion of body above the diaphragm is classified as "up" and below as "down". Cancers that occur above the diaphragm include lung cancer, breast cancer, etc. Cancers that occur below the diaphragm include stomach cancer, colon cancer, etc. In this case, the inventors have found that "cold" is associated the occurrence of cancer. Thus, if a patient is in a state of excess yin (up-cold/down-hot; left-cold/right-hot), he is likely to suffer cancer in organs above the diaphragm. Because the stomach is located on the left, if a patient is found to be "cold" in the left, he is also predicted to likely suffer cancer in the stomach.

On the other hand, if a patient is in a state of excess yang (up-hot/down-cold; left-hot/right-cold), he is likely to suffer cancer in liver, cervices, uterus, etc.

In addition, we found that leukemia and lymphoblastic cancers are also indicated by excess yang.

Application in Weight Loss

Obesity has become an epidemic in the developed countries and has been identified as a major risk factor in various diseases such as diabetes, cardiomyopathy, etc. We have discovered that obesity also exhibits a vitalimetrics pattern that can be used in tailoring a vitalimetrics-guided personalized treatment plan. In one embodiment, we first determine the vitality state deviation (excess yin or excess yang) of a patient. Once the direction of vitality imbalance is determined, we can then prescribe a personalized diet therapy to nurture the patient's vitality state back to its centered state. For example, if a patient is determined to suffer from an excess-yin obesity, a "yang" diet is prescribed. In one embodiment, the "yin-yang" characteristics of food is assigned as according to the TCM classic the Outline of Herbal Medicine ("Ben Cao Gang Mu"), arguably one of the earliest neutraceutics work. Many of the herbs described in the classic are in fact everyday food. This is in keeping with the systems concept that we are in constant dynamic balance with our surrounding, thus, the distinction between food and medicine is really only a matter of semantics.

One regimen we have prescribed for our overweight patient is a diet of 300-400 g cooked boneless meat per day pretreated with herbs. After each meal, liquid intake is strictly forbidden for 6 hours. If the patient is thirsty, little hot water can be used to rinse the mouth.

It should be noted that during treatment period, warm water is recommended for all water intake. This will prevent the rebound of body weight after successful treatment.

A Web-based Vitalimetrics Healthcare Delivery System

There are two key components for a system of the present invention: (1) a monitoring device comprising vitality sensors capable of concurrently measuring symmetric vital signs and environmental sensors for sensing ambient environmental conditions; and (2) a web-based processing server to receive and process the measurements from the vitality sensors.

The vitality sensors are preferably ones that can measure pulse rate and body temperature, ambient temperature, ECG, blood pressure, blood oxygen content, and can transmit the measurements wirelessly to a central server. Measurement of environmental conditions preferably incorporates GPS location information. The monitoring device is preferably equipped with an information displaying means such as LCD displays for displaying heart-rate, blood pressure, time, network status, body temperature, ambient temperature, and etc.

Figure 2:
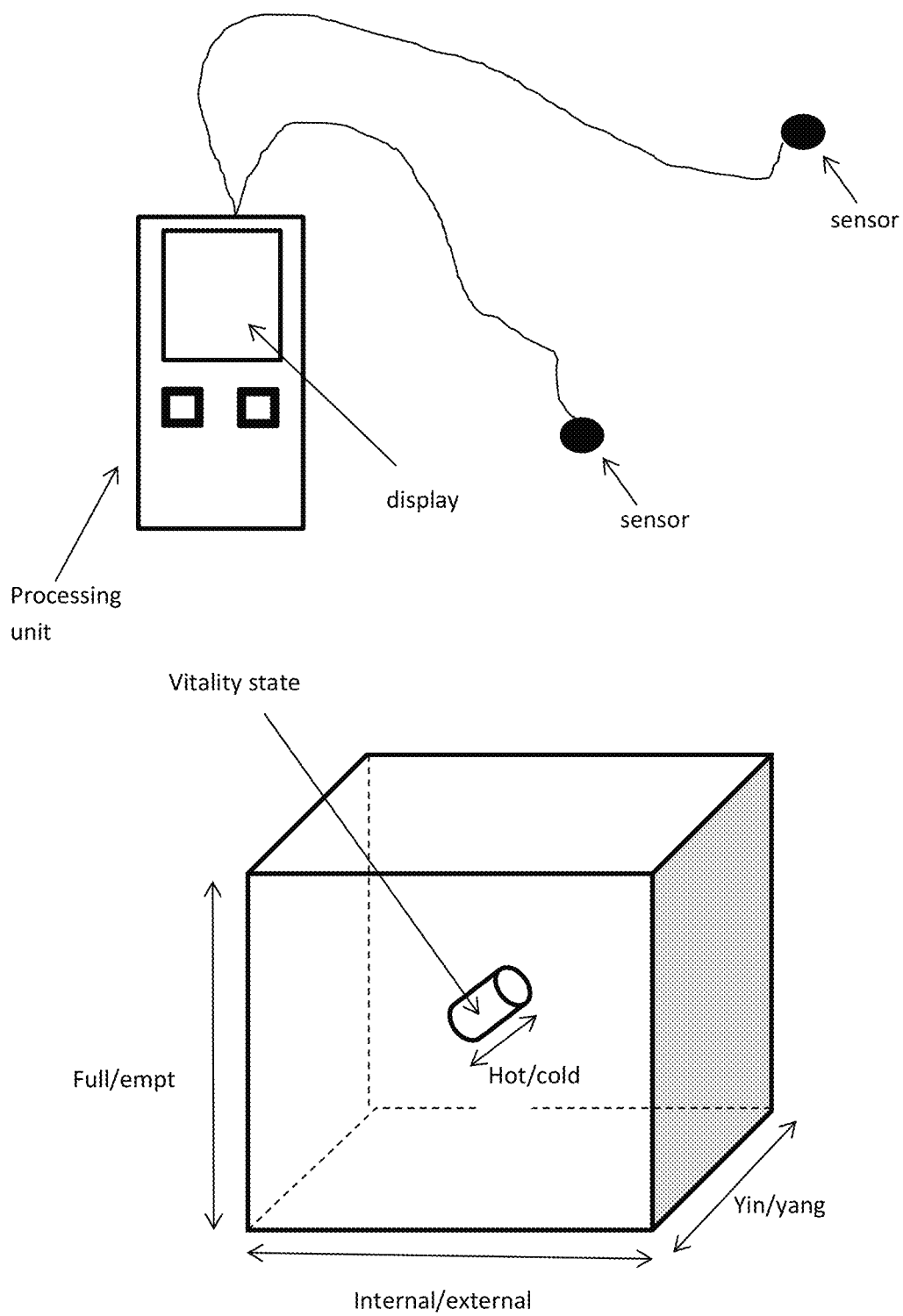
FIG. 2 upper panel shows an exemplary embodiment of a monitoring device having the capability of concurrently measuring vital signs from symmetric counterparts of a person. Lower panel shows an exemplary embodiment of a four-dimensional hyperspace representation indicating a vitality state as determined by the quantification of symmetric vital signs according to the Eight Princiles of TCM.
Figure 3:
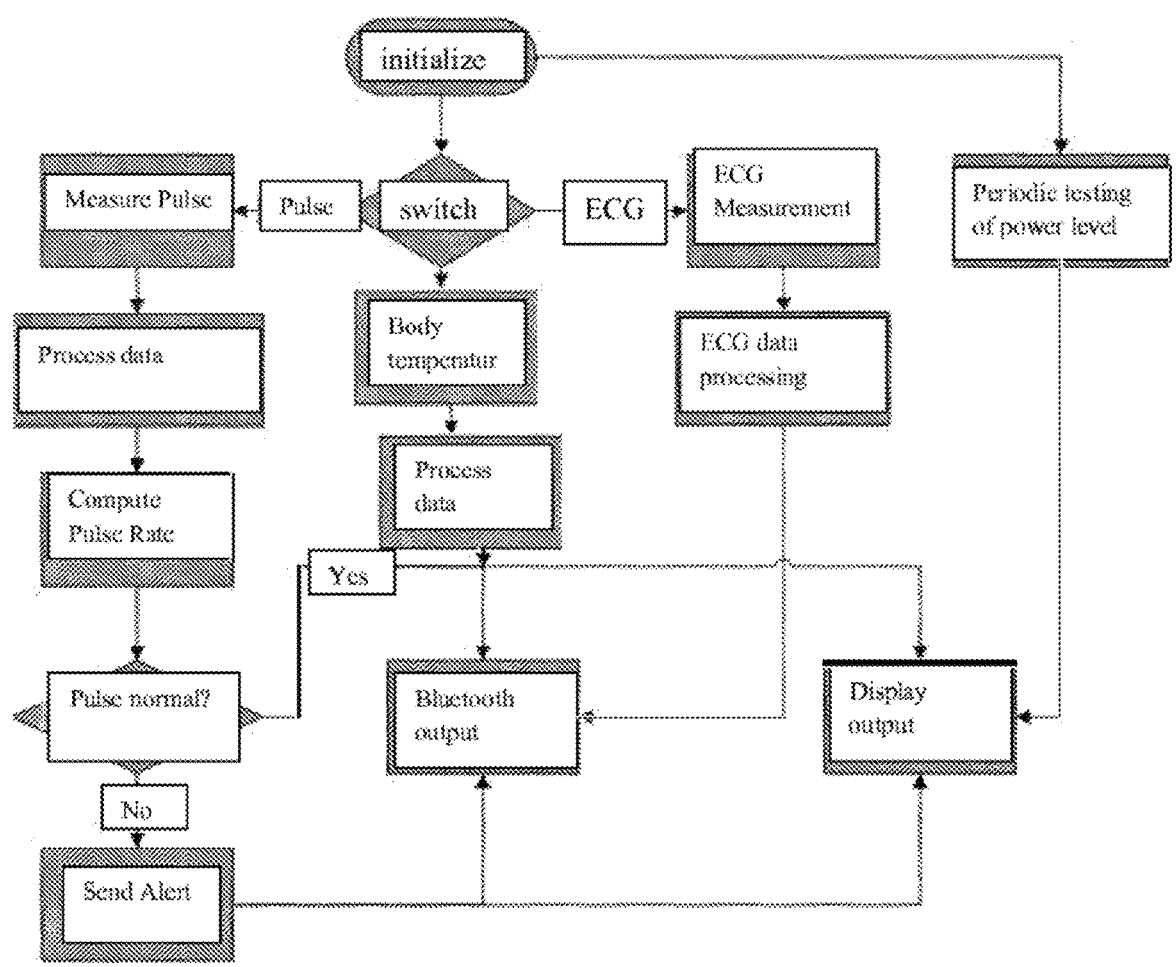
FIG. 3 shows an exemplary flowchart illustrating the internal operation of a monitoring device of FIG. 2.

FIG. 2 shows an exemplary embodiment of a monitoring device which incorporates the functionality of concurrent ECG and pulse rate measurement. FIG. 3 shows a flowchart illustrating the internal operating logics of the device.

The server is preferably configured to have a location-based service capability. For example, data received from the monitoring device can be directly mapped to an interactive map which displays the time/location tagged vitalimetrics measurements of the patient.

In this example, the web service employs an interactive interface to conduct patient interview and gather medical information about the patient. The exemplary questionnaire consists of more than 100 questions gathering information about multiple aspects of the patient's health and environment. An exemplary vitalimetrics measurement instruction is also provided through the website for users to take measurements at his/her convenience. The vitalimetrics are tracked over a period of time. In essence, the web application acts as a personal assistant to keep track of a patient's vitality state over time, and identify factors that may contribute to the disharmony in the patient.

In this way, the web portal provides a self-help tool for consumers to apply the methods of the present invention to maintain and improve their health. A user to this service will have his vitality states monitored over a long period of time. The more data collected, the better predictions the service can provide the user. Thus, the user may be able to see the activities and habits that contribute to changes in his vitality state, thereby, making lifestyle decisions to avert a catastrophic change or seek appropriate remedies to mitigate the disharmony.

In conjunction with the self-help features of the web service, a franchising model may be employed to enlist local clinics as service providers. By utilizing the quantitative methods described herein, a standardized practice may be established. In this new healthcare delivery paradigm, diagnosis of disease condition and treatment prescription will be guided by quantitative evidences, making the practice more transparent, and the training of service providers more uniform.

Another advantage of this paradigm is that new technologies may now be more easily integrated into practice. For example, wireless technology may now be employed to monitor a patient's vitality state around the clock, and record the patient's activities so that a close correlation between events and vitality state changes may be established.

Applications in Environmental Design

The systems approach of the present invention also lends itself to considerations about environmental influences on a person's health. For example, solar energy is the main energy driving life processes on earth. Yet the effect of solar energy on personal health has not been well considered in western medicine. In contrast, holistic medicine such as TCM theory does not consider human health independent of the environment. One fundamental tenant of TCM is that human health must be understood from the interactions among heaven, earth, and man. Thus, from the place we live to the food we eat, these variables are all taken into consideration in the formulation of TCM theories. Utilizing the methods and tools of vitalimetrics described herein, personalized design of environmental conditions conducive to health may be achieved.

For instance, utilizing vitalimetrics analysis, the web service described above may now offer personalize advices on a range of lifestyle issues that may affect health, including where to live, what to eat, and how to feel. Thus, under this new paradigm, treatment modalities may include environmental therapy, food therapy, dress therapy, herbal therapy, acupuncture therapy, or any other forms of therapy that have a known causal-relationship to affecting symmetric vital sign differences.

In one example, we consider the anisotropic temperature distribution in a modern housing. Temperature in most modern housing are controlled by central AC systems. Because of this active control, ambient temperature is rarely in equilibrium, and the temperature in the room may exhibit a vertically and/or horizontally stratified temperature zones. During the winter, when hot air is introduced from the ceiling vents, the room is hotter towards the ceiling and colder towards the floor. Therefore, according to vitalimetrics, a person who is in a vitality state of up-hot/down-cold may suffer ill effect for prolonged exposure that such environment, as it will acerbate the disharmony. On the other hand, such environments may benefit patients who are in a state of excess yin (left-cold/right-hot; up-cold/down-hot).

In high-rise buildings, the distribution of solar energy is also anisotropic both in the vertical direction and the horizontal direction. Thus, the principle of vitalimetrics may also be utilized to guide the selection of an unit optimal for a person in a predetermined vitality state.

Those skilled in the art will also readily recognize that architecture design of hospitals and residences may also be guided by taking the intended users' personal vitality state into consideration. In particular, hospital rooms may incorporate environmental control technologies to adjust the environment according to the patient's vitality state to benefit recovery of the patient. Computerized optimal AC temperature selection may also be devised to take into account the various factors affecting the anisotropy of temperature/radiation distribution in a room (e.g. the temperature in the unit above and below, the duration of solar exposure of the unit, etc.).

Application of Vitalimetrics to the Control of Water Consumption

The quantity of water consumed, the temperature and quality of the water are important factors affecting internal temperature differences of a person. Not enough water may cause blood to thicken leading to a rise in body temperature, and vice versa. Thus, a vitalimetrics-guided personal drinking prescription may be offered to a patient. Prescription of such programs may also be included in the web service described above.

In a preferred embodiment, water above 60° C. is consider to be "yang" and water below 60° C. is considered to be "yin". For patients whose vitality state deviate towards the yin direction, consumption of warm water at 60° C. or above is recommended.

Example Patient Case 1

Female patient age 56, height 163 cm, weight 68.5 kg. Patient seeking treatment for over-weight.

A base-line vitality state was determined over a 10 day period as described above. The patient was found to have negative $\Delta T=-0.35°$ C.

According to the lunar calendar assignment commonly used in TCM, the time that the vitality state was measured corresponded to gut, thus, the patient is also diagnosed with a deficiency in gut.

A vitality state guided treatment consisting of acupuncture, herbal remedy, water intake portioning, diet, and exercises was prescribed to address the imbalance.

After the treatment, the patient has lost 6.5 kg. The treatment was terminated when her vitality state has returned to $\Delta<0.3$.

Example Patient Case 2

Male patient, age 61, height 180 cm, weight 80 kg.

The patient seek help with diabetes (blood sugar on empty stomach is 10 mmol/L).

A base-line vitality state was determined. The patient was found to have a negative $\Delta T=-0.4°$ C.

Lunar calendar assignment indicates that the heart is also deficient.

A vitality state guided treatment consisting of acupuncture, herbal remedy, exercise, water and diet was prescribed.

After the treatment, the patient's blood sugar level was reduced to 8 mmol/L.

The Effect of Environmental Conditions

For every 1° C. increase in the average atmospheric temperature, there will be a corresponding 0.038° C. change in body temperature. When the surrounding atmospheric temperature is in the range of 10-25° C., for every 10° C. increase in the ambient temperature, there will be a corresponding decrease in calorie burn rate of 2.5-3 kcal/hour/m². On the other hand, there is very little increase in calorie burn rate when ambient temperature decreases.

Atmospheric temperature at a given geographic region is related to the amount of solar energy received at that region. The amount of solar energy received at a given geographic region, in turn, is related to the latitude of the region. For every degree increase in latitude from the equator, there is a corresponding 1.37° C. decrease in atmospheric temperature. Lower temperature has been found to be associated with longevity in life-span. This relationship indicates that temperature is a very strong environmental factor that can directly influence a person's state of health. Human body's metabolism is optimal when ambient temperature is in the range of 20-30° C. When ambient temperature falls below 20° C., oxygen consumption will increase. At 10° C., the increase in oxygen consumption is about 67%. But when temperature is in the range of 31-37° C., oxygen consumption actually shows a saddle pattern, reaching a minimum at 35° C. and increasing again at 38° C. At 40° C., a 12% increase was found. When temperature is at 50° C., oxygen consumption reaches 66.5%. The relationship between metabolic rate and ambient temperature clearly shows that there is a definitive, predictable, and measureable effect of ambient temperature on body's internal energy balance and consumption.

Similarly, other environmental factors such as moisture level, wind level, rain level, etc., can all affect the body's internal energy balance and metabolic rate in predictable and measureable patterns. Knowing how a particular environmental condition effects a person, and his current state of symmetric health, one can then device a treatment protocol which prescribes changes in environmental conditions to effect a movement of the person's vitality state towards a balanced state, thereby, restoring health in the person.

Example Patient Case 3

The present invention may be applied to monitoring the wellbeing or health state of a patient. It can also be used to compare the effectiveness of a treatment method by comparing the vitalimetric measurements before and after treatment.

Subject: Female. Age: 36. Complains feeling sick and lethargic from working too hard. Frequently catches cold, afraid of cold year around, suffering from back pain. Since puberty have always felt abdominal pain when menstruating. Family doctor diagnosed as mild thalassemia, left thyroid cyst, uterine fibroid. severe hyperplasia of breast hyperplasia. Cardiologist diagnosed as Mild tricuspid regurgitation, left ventricular regurgitation. Hepatobiliary specialist diagnosed as mild fatty liver, moderate enlargement of the spleen.

First night monitor −0.42. First ten-day average temperature −0.21, 1. The sign of the symmetric temperature difference remained the same for morning and night for ten days. This indicates that the monitoring method is generating consist measurements. As treatment method begins to improve the health state of the patient, the symmetric temperature begins to turn positive. However, no significant changes were observed in the symptoms. This indicates that our method is measuring some fundamental changes in the health state of the patient that cannot be readily observed by observable symptoms.

Using the symmetric temperature differences as a guide, when a particular treatment method results in positive changes, it should be continued. Whereas whenever a treatment method results in a negative change in the symmetric temperature difference, it should be stopped. Treatment methods that can both alleviate symptoms and result in positive symmetric temperature differences are the best courses of treatment. This is the fundamental approach of using vitalimetrics to select and improve therapeutic regiments at an individual level. It therefore enables true personalized medical treatment plan.

This particular patient began to show improvement in her back pain on September 11. Her period came on September 16 and experienced significant reduction in abdominal pain. At this time, her symmetric temperature difference was −0.02.

| Date | Time | Left | Right | ΔT | Time | Left | Right | ΔT |
|---|---|---|---|---|---|---|---|---|
| 7, 30a | | | | | 23 | 36 | 36.42 | −0.42 |
| 7, 31 | 7, 31 | 36.24 | 36.51 | −0.27 | 22.5 | 36.23 | 36.55 | −0.32 |
| 8, 1 | | | | | 22.5 | 36.08 | 36.46 | −0.38 |
| 8, 2 | 7a | 36.1 | 36.08 | 0.02 | 22.5 | 36.1 | 36.38 | −0.28 |
| 8, 3 | 7a | 36.1 | 36.1 | 0 | 22.5 | 36.08 | 36.48 | −0.4 |
| 8, 4 | 7, 15 | 36.14 | 36.15 | −0.01 | 22.5 | 36.65 | 36.55 | 0.1 |
| 8, 5 | 8 | 36.1 | 36.25 | −0.15 | 23 | 36.77 | 36.75 | 0.02 |
| 8, 6 (六) | 8 | 36.33 | 36.63 | −0.3 | 22.5 | 36.36 | 36.72 | −0.36 |
| 8, 7 | 7, 38 | 36.34 | 36.54 | −0.2 | 22.5 | 36.64 | 36.85 | −0.21 |
| 8, 8 | | | | | 22.5 | 37.1 | 36.95 | 0.15 |
| | | | | | | 36.401 | 36.611 | −0.21 |
| 8, 9 肾七/1 | 7 | 36.2 | 36.56 | −0.36 | 22.5 | 36.58 | 36.87 | −0.29 |
| 8, 10 | 7.15 | 36.59 | 36.62 | −0.03 | 22.5 | 36.66 | 36.88 | −0.22 |
| 8, 11 | 7.15 | 36.44 | 36.54 | −0.1 | 22.5 | 36.97 | 37.03 | −0.06 |
| 8, 12 | 7, 10 | 36.56 | 36.62 | −0.06 | 11 p | 36.53 | 36.85 | −0.32 |
| 8, 13 | | 36.53 | 36.7 | −0.17 | 22.5 | 36.92 | 36.95 | −0.03 |
| 8, 14 | 7.15 | 36.65 | 36.75 | −0.1 | 22.5 | 36.88 | 37.01 | −0.13 |
| 8-15 | 7.15 | 36.63 | 36.83 | −0.2 | 22.5 | 36.63 | 36.83 | −0.2 |
| 8-16 | 7:50 | 36.56 | 36.88 | −0.32 | 22:00 | 36.77 | 36.85 | −0.08 |
| 8-17 | 7:15 | 36.52 | 36.75 | −0.23 | 22:00 | 36.78 | 37.12 | −0.34 |
| 8-18 | 7:15 | 36.53 | 36.62 | −0.09 | 20:50 | 36.52 | 36.63 | −0.11 |
| | | 36.52 | 36.69 | −0.166 | | 36.72 | 36.90 | −0.178 |
| 8-19 | 7:25 | 36.32 | 36.35 | −0.03 | 20:30 | 36.32 | 36.59 | −0.27 |
| 20 | 9:00 | 36.35 | 36.60 | −0.25 | 23:00 | 36.56 | 36.61 | −0.05 |
| 七 21 | | | | | | | | |
| 8-21 | 9:15 | 36.45 | 36.58 | −0.13 | 23:00 | 36.56 | 36.61 | −0.05 |
| 8-22 | 7:00 | 36.27 | 36.38 | −0.11 | 22:15 | 36.56 | 36.61 | −0.05 |
| 8-23 | 7:30 | 36.24 | 36.48 | −0.24 | 22:30 | 36.72 | 36.68 | 0.04 |
| 8-24 | 7:30 | 36.35 | 36.50 | −0.15 | 22:30 | 36.60 | 36.65 | −0.15 |
| 8-25 | 7:30 | 36.16 | 36.21 | −0.05 | 23:00 | 36.45 | 36.70 | −0.25 |
| 8-26 | 7:30 | 36.07 | 36.30 | −0.23 | 0:00 | 36.27 | 36.57 | −0.30 |
| 8-27 | 7:30 | 36.05 | 36.28 | −0.23 | 22:30 | 36.65 | 36.71 | −0.06 |
| 8-28 | 8:30 | 36.29 | 36.37 | −0.08 | 22:00 | 36.75 | 36.80 | −0.05 |
| | | 36.26 | 36.41 | −0.15 | | 36.54 | 36.67 | −0.14 |
| 8-29 — | 7:30 | 36.07 | 36.28 | −0.21 | 22:30 | 36.50 | 36.65 | −0.15 |
| 8-30 | 7:30 | 36.35 | 36.45 | −0.10 | 22:30 | 36.54 | 36.66 | −0.12 |
| 8-31 | 7:30 | 36.27 | 36.23 | 0.04 | 22:30 | 36.50 | 36.52 | −0.02 |
| 9-1 | 7:30 | 36.06 | 36.14 | −0.08 | 22:30 | 36.50 | 36.65 | −0.15 |
| 9-2 | 7:15 | 36.35 | 36.54 | −0.19 | 21:30 | 36.44 | 36.67 | −0.23 |
| 9-3 | 9:30 | 36.60 | 36.64 | −0.04 | 23:30 | 36.97 | 36.95 | 0.02 |
| 9-4 | 7:30 | 36.45 | 36.72 | −0.27 | 22:30 | 36.98 | 36.97 | 0.01 |
| 9-5 | 7:00 | 36.35 | 36.67 | −0.32 | 23:00 | 36.65 | 36.87 | −0.22 |
| 9-6 | 7:00 | 36.72 | 36.76 | −0.04 | 22:30 | 36.76 | 36.93 | −0.17 |
| 9-7 (10 | 7:00 | 36.74 | 36.84 | −0.10 | 22:30 | 36.67 | 36.58 | 0.09 |
| | | 36.40 | 36.53 | −0.13 | | 36.65 | 36.75 | −0.09 |
| 9-9 | 7:00 | 36.67 | 36.71 | −0.04 | 22:30 | 36.77 | 36.92 | −0.16 |
| 9-10 | 7:15 | 36.61 | 36.81 | −0.20 | 23:00 | 36.57 | 36.97 | −0.40 |
| 9-11 | 8:30 | 36.87 | 36.70 | 0.17 | 22:00 | 37.00 | 37.15 | −0.15 |
| 9-12 | 8:30 | 36.75 | 36.90 | −0.15 | 22:00 | 36.95 | 36.75 | 0.20 |
| 9-13 | 7:00 | 36.46 | 36.70 | −0.24 | 22:30 | 36.98 | 37.09 | −0.11 |
| 9-14 | 7:30 | 36.70 | 36.83 | −0.13 | 22:30 | 36.90 | 37.15 | −0.25 |
| 9-15 | 7:30 | 36.70 | 36.67 | 0.03 | 22:00 | 36.85 | 37.07 | −0.22 |
| 9-16 | 7:30 | 36.38 | 36.40 | −0.02 | 22:30 | 36.65 | 36.80 | −0.15 |
| 9-17 | 7:30 | 36.31 | 36.50 | −0.19 | 22:30 | 36.63 | 36.85 | −0.22 |
| 9-18 | | 36.35 | 36.37 | −0.02 | 21:30 | 36.7 | 36.71 | −0.01 |

What is claimed is:

1. A method of symmetric health state determination, monitoring, and intervention, comprising:
   measuring one or more symmetric vital signs of a subject by using a symmetric vital sign measuring device, wherein said symmetric vital sign measuring device comprises:
      at least one pair of sensors for measuring at least one vital sign as input for computing a symmetric vital sign value;
      a processing unit capable of continuously receiving sensor inputs and configured to perform the steps of:
         computing a time series of the symmetric vital sign values; and
         determining a vitality state vector in a multidimensional hyperspace by taking the symmetric vital signs as state variables for the vector, wherein the values of symmetric vital signs are computed by taking the difference between a pair of vital sign values from a pair of symmetric counter-part locations on the subject's body;
      a display unit for displaying the symmetric vital sign values and a representation of the vitality state vector,
      wherein said sensors and display unit are operatively linked to the processing unit; and
   determining a vitality state for the subject based on the symmetric vital signs.

2. The method of claim 1, wherein said at least one vital sign measured by the sensors is body temperature.

3. The method of claim 1, wherein said at least one vital sign measured by the sensors are selected from the group consisting of: body temperature, blood pressure, pulse rate, and a combination thereof, and wherein all vital signs are measured concurrently by the same symmetric vital sign measuring device.

4. The method of claim 1, wherein said step of determining a vitality state comprises:
   assigning a state of left-hot/right-cold when the symmetric vital sign has a positive value, and a state of left-cold/right-hot when the symmetric vital sign has a negative value.

5. The method of claim 4, further comprising:
   prescribing a health intervention regimen according to the vitality state of the subject, wherein said intervention regimen is selected from the group consisting of diet, exercise, living environment, and a combination thereof.

6. The method of claim 1, wherein said multidimensional hyperspace is a four-dimensional hyperspace having each of its four dimensions corresponds to one of the four opposite pairs in the Eight Principles of traditional Chinese medicine which consists of: yin/yang; intern/external, full/empty, and hot/cold.

7. A symmetric vital sign measuring device, comprising:
   at least one pair of sensors configured to measure one or more type(s) of vital signs concurrently from symmetric counter-parts of a subject's body; and
   a processing unit configured to continuously receiving sensor inputs from said sensors, and performing the steps of
      computing a symmetric vital sign value for each type of vital sign by taking the difference between the vital sign values from a pair of vital sign measurements measured concurrently at symmetric counter-parts of the subject's body;
      determining a vitality state vector in a multidimensional hyperspace by taking the symmetric vital signs as state variables for the vector, and
      outputting a time series for each type of symmetric vital sign; and
   a displaying unit for displaying the symmetric vital sign values and a representation of the vitality state vector.

8. The device of claim 7, wherein said sensors are temperature sensors capable of determining temperature to a tolerance of 0.2 ° C. or less.

9. The device of claim 7, wherein said sensors form a body sensor network operatively linked to a central processing unit via an electronic communication network.

* * * * *